United States Patent
Halskov et al.

(10) Patent No.: US 9,763,882 B2
(45) Date of Patent: Sep. 19, 2017

(54) COMPOSITION FOR THE TREATMENT OF FISTULA

(71) Applicant: FERRING B.V., Hoofddorp (NL)

(72) Inventors: Søren Halskov, Virum (SE); Mats Ekelund, Lund (SE)

(73) Assignee: Ferring BV, Hoofddorp (NL)

( * ) Notice: Subject to any disclaimer, the term of this patent is extended or adjusted under 35 U.S.C. 154(b) by 0 days.

(21) Appl. No.: 14/348,379

(22) PCT Filed: Oct. 3, 2012

(86) PCT No.: PCT/EP2012/069513
§ 371 (c)(1),
(2) Date: Mar. 28, 2014

(87) PCT Pub. No.: WO2013/050404
PCT Pub. Date: Apr. 11, 2013

(65) Prior Publication Data
US 2014/0288491 A1    Sep. 25, 2014

(30) Foreign Application Priority Data

Mar. 10, 2011 (EP) .................................. 1117148
Mar. 10, 2011 (EP) .................................. 11183665

(51) Int. Cl.
| | | |
|---|---|---|
| A61K 9/14 | (2006.01) |
| A61M 3/00 | (2006.01) |
| A61K 33/44 | (2006.01) |
| A61K 9/00 | (2006.01) |
| A61M 31/00 | (2006.01) |
| A61K 33/00 | (2006.01) |
| A61M 3/02 | (2006.01) |

(52) U.S. Cl.
CPC ............ *A61K 9/14* (2013.01); *A61K 9/0031* (2013.01); *A61K 33/00* (2013.01); *A61K 33/44* (2013.01); *A61M 3/005* (2013.01); *A61M 3/0279* (2013.01); *A61M 31/007* (2013.01); *A61M 3/0258* (2013.01); *A61M 3/0262* (2013.01); *A61M 2202/064* (2013.01); *A61M 2210/1067* (2013.01); *F04C 2270/041* (2013.01)

(58) Field of Classification Search
USPC ........................................................ 424/489
See application file for complete search history.

(56) References Cited

U.S. PATENT DOCUMENTS

| | | | |
|---|---|---|---|
| 4,657,108 | A | 4/1987 | Ward |
| 5,554,370 | A | 9/1996 | Uehara et al. |
| 5,562,901 | A | 10/1996 | Uehara et al. |
| 5,860,916 | A | 1/1999 | Pylant |
| 2006/0034825 | A1 | 2/2006 | Charron |
| 2014/0243794 | A1 | 8/2014 | Halskov et al. |

FOREIGN PATENT DOCUMENTS

| | | | |
|---|---|---|---|
| CN | 201082299 | * | 7/2008 |
| DE | 102009033400 | | 1/2011 |
| FR | 2094420 | | 2/1972 |
| GB | 507849 | | 6/1939 |
| GB | 1240392 | | 7/1971 |
| JP | 2005-089306 | | 7/2005 |
| WO | WO 2013050408 | | 4/2013 |

OTHER PUBLICATIONS

Norit (http://www.docstoc.com/docs/104751474/Norit-E-Supra-USP, accessed Mar. 22, 2015).*
Gross (Sexually Transmitted Diseases, Nov. 1999, vol. 26, No. 10, pp. 572-578).*
Mikhalovsky (Use of Hugh Surface Nanofibrous Materials in Medicine, p. 249 of Chapter 4.1.1 in Nanoengineered nanofibrous materials. Edited by Selcuk Guceri, Yury G. Gogotsi, and Vladimir Kuznetsov. vol. 169. Springer Science & Business Media, 2007).*
Translation of CN201082299, Jul. 9, 2008.*
International Search Report for PCT/EP2012/069513 mailed Nov. 5, 2012. 3 pages.
Database WPI Week 200529, Thomson Scientific, London, GB., AN 2005-277149 XP002669189.
Fukuda et al., "Oral Spherical Adsorptive Carbon for the Treatment of Intractable Anal Fistulas in Crohn's Disease: A Multicenter, Randomized, Double-Blind, Placebo-Controlled Trial," Am. J Gastroenterol., 2008, 1721-1729.
Reinisch et al., "AST-120 (Spherical Carbon Adsorbent) in the Treatment of Perianal Fistulae in Mild-to-Moderate Crohn's Disease: FHAST-1, a Phase 3, Multicenter, Placebo-controlled Study", Infamm. Bowel Dis., 2014, 20(5), 872-881.
International Search Report and Written Opinion in International Application No. PCT/EP2012/069518, dated Jan. 17, 2013, 14 pages.
Fukuda et al., "Oral Spherical Adsorptive Carbon for the Treatment of Intractable Anal Fistulas in Crohn's Disease: A Multicenter, Randomized, Double-Blind, Placebo-Controlled Trial," Am. I Gastroenterol., 2008, 1721-1729.

* cited by examiner

*Primary Examiner* — Devang Thakor
(74) *Attorney, Agent, or Firm* — Fish & Richardson P.C.

(57) ABSTRACT

A composition for use in the treatment of fistula, the composition comprising activated carbon.

41 Claims, 6 Drawing Sheets

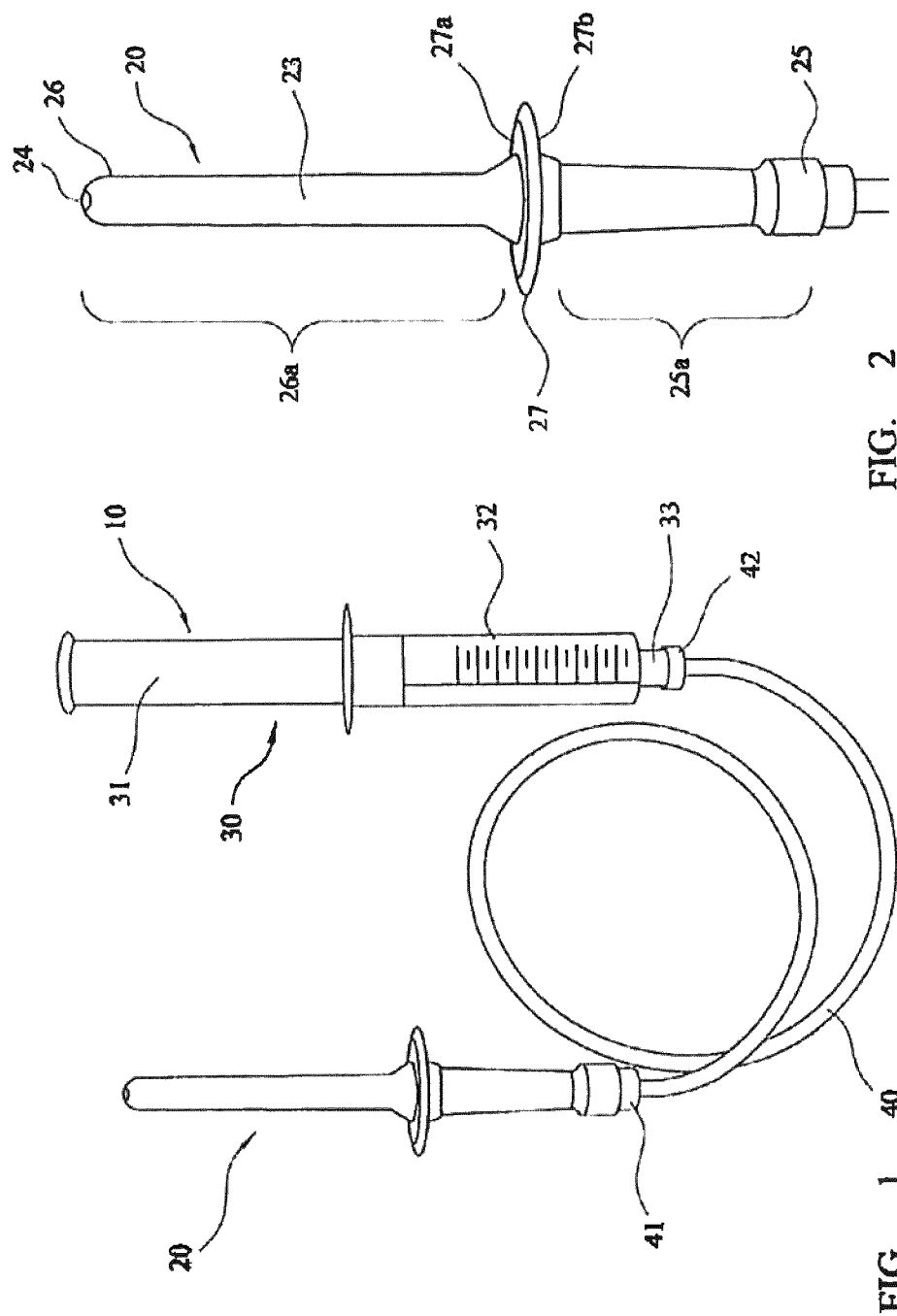

COMPOSITION FOR THE TREATMENT OF FISTULA

CROSS REFERENCE TO RELATED APPLICATIONS

This is a U.S. National Phase application under 35 U.S.C. §371 of International Patent Application No. PCT/EP2012/069513, filed Oct. 3, 2012, which published as WO2013/050404, and which claims the priority of European Patent Application No. 11183665.6 filed on Oct. 3, 2011 and British Patent Application No. 1117148.5 filed on Oct. 3, 2011. The foregoing applications and WO2013/050404 are hereby incorporated by reference in their entirety.

The invention relates to a pharmaceutical composition comprising activated carbon particles for the treatment of fistula, for example rectal or anal fistula.

BACKGROUND

A fistula is an abnormal conduit or connection between bodily organs or vessels that do not usually connect. Fistulas or fistulae can form in many parts of the body. Anal fistula and rectal fistula are conditions in which tubes form between a sufferer's rectum and intestines, or other internal organs, or between a sufferer's rectum and the external skin adjacent to the sufferer's anus. For example, fistulas situated high in the anus (high anal fistula) may connect with the urinary tract, and fistulas situated low in the anus (low anal fistula) may, in women, pass into the vagina. In addition to significant pain, rectal and anal fistulas commonly become infected and accumulate pus. Furthermore, such fistulas can allow the leakage of fecal matter from the rectum.

Anal and rectal fistulas may form as a result of disease or infection. For example, anal fistulas may arise if a sufferer's anal glands become blocked, thereby forming an abscess that points through from the rectum to the skin surface in the anal region. The growth of fistulas may be accelerated, and fistulas themselves may be maintained, by a local build up of substances which cause irritation (e.g. in the rectum).

Anal and rectal fistulas may be treated by surgical procedures. Such procedures are undesirable, however. One potential side-effect of the surgical procedure to treat fistula is an increased probability that a patient will develop anal incontinence in the years following the surgery. The use of glue (e.g. fibrin glue) and plug procedures reduces the likelihood of anal incontinence, but nevertheless surgical procedures are generally relatively expensive compared to medication, and are generally less convenient and less preferable to the patient.

Activated carbon has been proposed for use in the treatment of rectal and anal fistulas. However, there are a number of problems associated with the use of activated carbon for this purpose. Activated carbon is typically supplied as an extremely fine powder having a high surface area. The European Pharmacopoeia describes activated carbon as a black, light powder free from grittiness. There are, however, problems associated with handling such a powder as the fine scale of the powder particles means the activated carbon tends to contaminate its immediate surroundings with a fine powder dust of activated carbon. These fine powders of activated carbon may have particles sizes predominately smaller than 170 mesh (predominantly smaller than 89 µm), i.e. in which most of the particles in the powder would pass through a sieve of mesh size 170 and in which the average particle size is considerably smaller than this. The inventor of the present application investigated a typical sample of fine activated carbon powder using a microscope and found that the particles were smaller than 20 µm in diameter. Such a powder is, therefore, inherently dirty and difficult to handle. A fine powder also does not flow easily, and it is difficult to administer a dry dose of activated carbon. A dry dose of activated carbon is a dose of activated carbon that has been maintained in dry conditions until the point of delivery.

To alleviate some of the handling problems, activated carbon has previously been prepared for oral administration. However, orally administered activated carbon must pass through a patient's entire digestive system before it reaches the rectal region and in doing so a large (and unpredictable) proportion of the carbon will have adsorbed various chemicals and lost its activity, or otherwise loses its activity, depending on various factors such as amount of food in gut, inter patient variations and day to day variations. By increasing the dose of orally administered activated carbon it may be possible to increase the proportion of carbon that reaches the rectum in an activated state. However, activated carbon absorbs many essential chemicals and nutrients on passing through the patient's digestive system and the long-term administration of large oral doses of activated carbon over a prolonged period is therefore undesirable.

Activated carbon has been prepared for rectal administration by pre-mixing to form a suspension with a liquid (e.g. propylene glycol). The problem with such suspensions is that the carbon may lose its activity very quickly due to adsorption of components of the liquid by the activated carbon. For example, experiments have compared the amount of phenazone adsorbed per 100 g activated carbon suspended in either water or 50% water/propylene glycol. The results showed that in water, activated carbon adsorbed 43 g phenazone per 100 g carbon; in 50% propylene activated carbon adsorbed only 16 g per 100 g phenazone. Clearly, the activity of the carbon is markedly reduced by adsorption of the propylene glycol. Suspensions of activated carbon, therefore, need to be used shortly after preparation and have little practical shelf-life.

Activated carbon has also been coated or otherwise formulated to allow it to pass through a patient's digestive system when taken orally. For example, U.S. Pat. No. 5,554,370 discloses capsules for oral administration of activated carbon. It may be difficult to prepare a coating that accurately dissolves to release the activated carbon only once it has passed into a patient's rectum. Furthermore, such coating or encapsulation may itself reduce or eliminate the activity of the carbon (e.g. in the same manner as described above for suspensions) and thereby may reduce the effectiveness of such coated particles for the treatment of rectal and anal fistulas.

JP2005-089306 discloses a suppository comprising activated carbon. The suppository is formulated with other excipients (e.g. gelatine, wax such as Witepsol W35) which effectively coat the activated carbon. As discussed above, coating reduces or eliminates the activity of the carbon and thereby may reduce the effectiveness of such coated particles for the treatment of rectal and anal fistulas. Further, suppositories which include activated carbon may not achieve predictable or effective administration of activated carbon particles for several reasons. Firstly, administration by suppository requires effective insertion by the patient to the required depth, which is not always achieved, and may be unhygienic. Further, therapeutic benefit requires effective capillary flow of activated carbon particles from the rectal cavity which may not be achieved because of the weight of the activated carbon particles and/or inter-patient variation of mucosal secretion; the activated carbon may remain at the base of the rectum and therefore not reach the site of the fistula. Thus, suppositories including activated carbon are far from ideal. JP2005-089306 also discloses an example of an enema formulation. However, as indicated above, enema suspensions tend to have poor shelf life and reduced activity due to adsorption of components of the liquid by the activated carbon. The inclusion of preservatives in enema suspensions of activated carbon (e.g. suspensions in water) to enhance shelf life is inappropriate because the preservative would be adsorbed by the activated carbon, thereby reducing activity of the activated carbon and leaving the water phase unprotected.

Thus, there is a need for compositions for (use in) the treatment of fistula which retain their pharmaceutical activity prior to administration (i.e. have good shelf life), have improved handling qualities, and are associated with predictable and repeatable dosing and good patient compliance.

The applicants have surprisingly found that it is possible to formulate and administer activated carbon which is dust free [for example activated carbon of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm)], as a dry powder or dry dose. Formulation of activated carbon as a dry powder prevents deactivation of the carbon (there is no adsorption of other excipients or components of the administration vehicle on the activated carbon); allows effective administration without the problems associated with rectal suppositories and oral administration (particles of this size may be administered rectally as a powder, and there is little or no loss of activity due to adsorption in the gut); and has other advantages in terms of cleanliness and contamination (particles of this size are not dusty).

According to the present invention there is provided a composition (e.g. a pharmaceutical composition) for use in the treatment of fistula, the composition comprising a dry powder (a dry dose) of activated carbon which is dust free. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm).

Thus, according to the present invention there is provided a composition (e.g. a pharmaceutical composition) for use in the treatment of fistula, the composition comprising a dry powder (a dry dose) of activated carbon of particle size 0.001 to 1 mm, for example 0.01 to 1 mm, for example 0.02 to 1 mm. Preferably, the activated carbon is of particle size 0.05 to 1 mm, for example 0.1 to 0.5 mm, for example 0.15 mm to 0.4 mm, for example 0.2 to 0.3 mm. The activated carbon may be of particle size 0.15 to 1 mm. Preferably the activated carbon is of average particle size 0.05 to 1 mm. Preferably the activated carbon is of average particle size 0.15 to 0.3 mm. Preferably the composition (e.g. pharmaceutical composition) is for use in the treatment of rectal or anal fistula. Preferably the dry powder (dry dose) of activated carbon is free of dust or substantially free of dust.

According to the present invention in a further aspect there is provided a composition (e.g. a pharmaceutical composition) for use in the treatment of fistula, the composition comprising a dry powder (a dry dose) of activated carbon wherein 85% or more of the activated carbon particles have diameter in the range from 0.089 mm to 0.3 mm. The activated carbon may be activated carbon wherein 85% or more of the activated carbon particles have diameter in the range from 0.104 mm to 0.297 mm. The activated carbon may be activated carbon wherein 85% or more of the activated carbon particles have diameter in the range from 0.125 mm to 0.297 mm. A particularly preferred activated carbon is activated carbon wherein 85% or more of the activated carbon particles have diameter in the range from 0.152 mm to 0.297 mm. Preferably the composition (e.g. pharmaceutical composition) is for use in the treatment of rectal or anal fistula.

According to the present invention in a further aspect there is provided a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm) for use in the treatment of fistula, or for use in the manufacture of a medicament for the treatment of fistula. The activated carbon may be of particle size 0.05 to 1 mm. Preferably the activated carbon is of particle size 0.15 to 0.3 mm. The activated carbon may be of average particle size 0.15 to 1 mm. Preferably the fistula is rectal or anal fistula. Preferably the dry powder (dry dose) of activated carbon is free of dust or substantially free of dust.

According to the present invention in another aspect there is provided a method of treatment of fistula comprising a step of administering (to a subject in need thereof) a pharmaceutically effective amount of a composition comprising a dry powder (a dry dose) of activated carbon of particle size 0.001 to 1 mm, for example 0.02 to 1 mm, preferably 0.05 to 1 mm (for example 0.1 to 0.5 mm, for example 0.15 mm to 0.4 mm, for example 0.2 to 0.3 mm). The activated carbon may be of particle size 0.15 to 1 mm. Preferably the activated carbon is of particle size 0.15 to 0.3 mm. Preferably the treatment is treatment of rectal or anal fistula.

According to the invention in an aspect there is provided a composition for use in the treatment of fistula, the composition comprising a dry powder of activated carbon of particle size 0.001 to 1 mm, for example 0.02 to 1 mm, preferably 0.05 to 1 mm, wherein the composition is for administration (to be administered) rectally as a dry powder. The activated carbon may be of particle size 0.15 to 1 mm. The activated carbon may be of average particle size 0.15 mm to 0.3 mm.

According to the invention in an aspect there is provided a composition for use in the treatment of fistula, the composition comprising a dry powder of activated carbon of particle size which is dust free, wherein the composition is for administration (to be administered) rectally as a dry powder. Preferably the dust free carbon is of particle size 0.02 to 1 mm, preferably of particle size 0.05 to 1 mm (e.g in the form of "macroparticles" of particle size from approximately 0.15 mm to 0.3 mm, e.g. 0.2 to 0.3 mm).

The composition (e.g. pharmaceutical composition) comprises a dry powder (dry dose) of activated carbon. Herein the terms "dry dose" and "dry powder" of activated carbon mean activated carbon that has been maintained in dry conditions until the point of delivery to the patient's body. The use of a dry powder (dry dose) of activated carbon particles means the adsorbtive capacity of the activated carbon is retained and maintained until administration.

Preferably the composition or pharmaceutical composition is for rectal administration. The composition or pharmaceutical composition may comprise 450 µg to 10 g activated carbon. Preferably the composition or pharmaceutical composition comprises 450 µg to 5 g activated carbon. In an example, the composition or pharmaceutical composition comprises 450 µg to 1 g activated carbon. In another example, the composition or pharmaceutical composition comprises 950 µg to 2.5 g activated carbon. In another example, the composition or pharmaceutical composition comprises 950 μg to 1.3 g activated carbon. In an example the composition or pharmaceutical composition comprises 1.2 g activated carbon. In an example the composition or pharmaceutical composition comprises 1.2 g (±10%) activated carbon. In other words, the composition or pharmaceutical composition may comprise 1.08 to 1.32 g activated carbon.

The composition or pharmaceutical composition may comprise a dose (e.g. a unit dose or single dose) of 450 μg to 10 g activated carbon. Preferably the composition or pharmaceutical composition comprises a dose (e.g. a unit dose or single dose) of 450 μg to 5 g activated carbon. In an example, the composition or pharmaceutical composition comprises a dose (e.g. a unit dose or single dose) of 450 μg to 1 g activated carbon. Doses of 450 μg to 1 g activated carbon may be suitable for the treatment of children. In another example, the composition or pharmaceutical composition comprises a dose (e.g. a unit dose or single dose) of 950 μg to 2.5 g activated carbon. In another example, the composition or pharmaceutical composition comprises a dose (e.g. a unit dose or single dose) of 950 μg to 1.3 g activated carbon. Doses of 950 μg to 2.5 g (e.g. of 950 μg to 1.3 g, e.g. doses of 1.1 g, 1.2 g etc.) activated carbon may be suitable for the treatment of adults. Preferably the composition or pharmaceutical composition is for administration 1, 2, or 3 times a day at the dose levels above. Preferably the composition or pharmaceutical composition is for administration after the, or each, bowel movement. The composition or pharmaceutical composition may be for treatment of rectal or anal fistula in a patient with Irritable Bowel Syndrome or Crohns disease. It will be appreciated that dose administration to a patient with Irritable Bowel Syndrome or Crohns disease may be more frequent than 1, 2, or 3 times a day because bowel movements may be more frequent in such patients.

The activated carbon may be granular activated carbon.

Herein the term "particle size" means the width at the narrowest point of the activated carbon particle or granule (e.g the diameter for a spherical or roughly spherical particle).

Activated carbon (e.g. granular activated carbon) and its methods of manufacture is well known in the art and is available from, for example, Chemviron Carbon. Preferably the activated carbon is a pharmaceutical or medical grade activated carbon.

Activated carbon is designated by sizes such as 8×20, 20×40, or 8×30. A 20×40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). A U.S. Standard Mesh Size No. 50 sieve has openings of 0.297 mm; a No. 60 sieve has openings 0.251 mm; a No. 70 sieve has openings 0.211 mm; a No. 80 sieve has openings 0.178 mm; a No. 100 sieve has openings 0.152; a No. 120 sieve has openings 0.125 mm, a No. 140 sieve has openings 0.104 mm, and a No. 170 sieve has openings 0.089 mm. A notation for indicating particle size distribution using mesh size is to use + and − designations. A "+" before the sieve mesh indicates the particles are retained by the sieve, while a "−" before the sieve mesh indicates the particles pass through the sieve. This means that typically 90% or more of the particles will have mesh sizes between the two values. Thus, if the particle size of a material is described as −80/+170 (or could also be written −80+170), then 90% or more of the material will pass through an 80 mesh sieve and be retained by a 170 mesh sieve. Using the figures above, it can be seen that the resulting particles will have a range of diameters between 0.089 and 0.178 mm (89 and 178 micrometers). The activated carbon may be of particle size distribution −50/+120, wherein 90% or more of the activated carbon particles have diameter in the range from 0.125 mm to 0.297 mm. Preferably the activated carbon is of particle size distribution −50/+100, wherein 90% or more of the activated carbon particles have diameter in the range from 0.152 mm to 0.297 mm. Preferably the activated carbon is of particle size distribution −50/+80, wherein 90% or more of the activated carbon particles have diameter in the range from 0.178 mm to 0.297 mm. More preferably the activated carbon is of particle size distribution −50/+70, wherein 90% or more of the activated carbon particles have diameter in the range from 0.211 mm and 0.297 mm.

The activated carbon may be an activated carbon wherein 85% or more of the activated carbon particles have diameter in the range from 0.089 mm to 0.3 mm. The activated carbon may be activated carbon wherein 85% or more of the activated carbon particles have diameter in the range from 0.125 mm to 0.297 mm. A particularly preferred activated carbon is activated carbon wherein 85% or more of the activated carbon particles have diameter in the range from 0.152 mm to 0.297 mm.

It is preferred that the activated carbon particles are formed by grinding carbon material to the desired size. Ground activated carbon has an irregular particle shape and this irregular shape may be particularly suited to being cleanly delivered (e.g. from a delivery device, as described herein). The activated carbon may be in the form of spheronised or spherical particles. The activated carbon may be coated.

The (pharmaceutical composition) may be delivered into a patient's rectal cavity, e.g. using a device. One suitable device comprises a rectally-insertable cannula having a proximal opening, a distal opening, and a cavity defined through a body of the cannula between the proximal opening and the distal opening for containing the dose of pharmaceutical composition. An openable closure acts to close the proximal opening of the canula. Preferably, the cannula is of length 6 to 8 cm, e.g 7 cm. For example, a one-way valve may act to close the proximal opening of the cannula, or alternatively a suitable closure means such as a frangible seal that ruptures on the application of pressure may be used. A frangible seal, or similar ruptureable closure, could only be used one time, and would need to be replaced if the cannula is to be re-used. The device further comprises an actuation means for driving a volume of fluid (e.g. liquid such as water, or gas such as air) through the one-way valve (or alternative closure means) and the cavity to flush the dose of pharmaceutical composition out of the cavity through the distal opening of the cannula. The actuation means or actuator may comprise a suitable volume of liquid or may be loadable with a suitable volume of liquid for flushing the cavity. For example, the actuation means or actuator may have a chamber for holding a volume of liquid that may be filled with a suitable liquid prior to use of the device. A suitable liquid should be a liquid that does not influence the adsorptive capacity of the carbon and may be water or a medical solution, for example a saline solution. The skilled person will be aware of suitable liquids that can safely be injected into a patient's rectum. In another example, the actuation means or actuator may comprise a suitable volume of gas (e.g air) or may be loadable with a suitable volume of gas (e.g. air).

By containing the pharmaceutical composition within the cavity of the cannula, the activated carbon can be maintained separately from the liquid (if the fluid is a liquid) until the point of delivery; in other words the pharmaceutical composition is a dry dose or dry powder. As the activated carbon (the pharmaceutical composition) is stored in a dry condition it does not lose its activity for a considerable period of time and, therefore, the activity of the carbon particles is high as they are injected into the patient. Preferably, the driving liquid does not mix to a great extent with the activated carbon during delivery but merely forces the activated carbon out of the distal opening of the cannula and into a patient's rectum. The function of the liquid is to act like a piston to drive the carbon into the patient, and the liquid may therefore be referred to as a driving liquid or a propellant.

Preferably, the medicament consists of particles of activated carbon having an average particle size greater than 0.05 mm. For example, if the particle size is determined by sieving a portion of powder through a graded series of sieves, the average particles size determined in this way is preferably greater than 0.05 mm. If the average particle size is lower than 0.05 mm then the medicament may be difficult to handle, as it will be prone to forming an airborne dust. Such fine particles are difficult to wet and may also clump or agglomerate during storage and, therefore, may not flush from the cannula easily. The applicant's experiments indicate that if fine particles having average particle size lower than 0.05 mm are used, 20% to 50% of the particles (i.e. the dose) may be retained in the syringe and therefore not actually administered.

The applicants have found that if the activated carbon is of particle size 0.15 mm to 1 mm, it is preferred that the fluid (driving fluid) is a liquid (e.g. water). The applicants have surprisingly found that if the activated carbon is of particle size 0.05 mm to 0.15 mm, the fluid (driving fluid) may be a liquid (e.g. water) or a gas (e.g. air).

In addition to the preferred particle size ranges stated above, it is preferred that the activated carbon has a bulk density or apparent density of from 0.015 to 0.6 $g/cm^3$, for example from 0.4 $g/cm^3$ to 0.5 $g/cm^3$, preferably from 0.44 $g/cm^3$ to 0.45$g/cm^3$. Bulk density may be calculated according to the standard procedure set out in ASTM D2854. The bulk density may be from 0.15 to 0.05 $g/cm^3$.

The activated carbon particles are formed by grinding carbon material to the desired size.

Loading the cannula with the pharmaceutical composition may be an action undertaken by a patient. However, it may be convenient if the device is preloaded with the pharmaceutical composition. The pharmaceutical composition may, therefore, be loaded into the cannula cavity under controlled conditions and sealed at one end by the openable closure and at the other end by a sealing means. Such sealing means may, for example, be a removable seal that is removed by the user before delivery or a frangible seal that breaks on actuation. A suitable sealing means may be a cap or sheath that protects the external surface of the cannula, or at least of an insertable portion of the cannula. The sealing means may even be a second one-way valve that allows passage of the contents of the cavity to pass out of the cannula when the device is actuated.

The actuation means may be a manually-operated actuator for example a syringe or a bellows or a bulb. The manually-operated actuator is preferably capable of being filled with a driving liquid from a source of such liquid. For example, if the driving liquid is water then the water may be supplied as sterile water for injection in a container, such as a flask or a vial, and then transferred to an actuation means, such as a syringe, prior to use of the device. It is preferable, therefore, that the actuation means is removably coupleable from the device to allow it to be filled or loaded with the driving liquid and then coupled to the device in a suitable arrangement for forcing the driving liquid through the one-way valve into the cannula cavity. It may be advantageous for the actuation means to be an automatic actuator that delivers a volume of a driving liquid on, for example, the press of a button. For example the actuation means may be a motorised actuator that is operable to drive liquid from a source of liquid through the one-way valve and the cannula cavity to deliver the dose of particular pharmaceutical composition.

The device may comprise a flange or collar that extends radially outwards from an external surface of the cannula at a predetermined distance from the distal opening to determine the maximum depth of insertion of the cannula into the patient's rectum. Such a flange or collar presents a physical barrier that prevents or hinders a portion of the cannula proximal to the flange or collar from easily being inserted through a patient's anus. The flange or collar may also help provide a user with purchase on the cannula to allow the application of insertion force in the direction of a longitudinal axis of the cannula. For example, a user may apply a force on a proximal surface of a flange or collar in order to insert the cannula to a depth at which a distal surface of the flange or collar abuts the patient's anus.

The cannula may be preloaded with pharmaceutical composition in a controlled environment. In such circumstances the loaded cannula may be conveniently supplied as a disposable component containing a preloaded volume of pharmaceutical composition. Such a preloaded cannula could be attached to a device, the device could be activated to deliver the pharmaceutical composition, and then the spent cannula could be removed from the device and disposed of.

It may be convenient for a patient suffering from anal or rectal fistula to be supplied with a kit of parts for treatment of the disease comprising a device as described above. Thus, a further aspect of the invention may provide a kit for the treatment of (e.g. anal and rectal) fistula comprising a delivery device (e.g. as described above); a supply of activated carbon particles of particle size 0.001 to 1 mm, for example 0.02 to 1 mm, preferably 0.05 to 1 mm (for example 0.1 to 0.5 mm, for example 0.5 mm to 0.4 mm, for example 0.15 to 0.3 mm, for example 0.2 to 0.3 mm); and optionally a source of fluid (e.g. liquid) for flushing the activated carbon particles through the device. The activated carbon may be of particle size 0.15 to 1 mm. The delivery device is preferably a device for rectal delivery of activated carbon.

Preferably the activated carbon is of average particle size 0.15 to 0.3 mm. A still further aspect of the invention may provide a kit for the treatment of (e.g. anal and rectal) fistula comprising a delivery device (e.g. as described above); a supply of activated carbon particles wherein 85% or more of the activated carbon particles have diameter in the range from 0.089 mm to 0.3 mm (e.g. wherein 85% or more of the activated carbon particles have diameter in the range from 0.152 mm to 0.297 mm); and optionally a source of fluid (e.g. liquid) for flushing the activated carbon particles through the device.

The fluid for flushing the activated carbon particles could be any suitable liquid. Preferably the liquid is a liquid that does not influence the adsorptive properties of the activated carbon particles and is safe for injection into a patient's rectum. The skilled person will be aware of many such suitable liquids but as an example the liquid may be sterile water, for example water for injection, a salt solution, etc. The fluid may be a gas (e.g. air).

As described above, it may be advantageous for the activated carbon particles to be preloaded into disposable, rectally-insertable, cannulas. Thus, the invention may further provide a kit for the treatment of anal and rectal fistula comprising a disposable, rectally-insertable, cannula including (e.g. a single dose of) activated carbon particles of particle size 0.001 to 1 mm, for example 0.02 to 1 mm, preferably 0.05 to 1 mm [for example 0.1 to 0.5 mm, for example 0.5 mm to 0.4 mm, for example 0.2 to 0.3 mm]; and optionally an activation means that can be filled or loaded with a volume of driving fluid (e.g. liquid). The activated carbon may be of particle size 0.15 to 1 mm. Preferably the activated carbon is of average particle size 0.15 to 0.3 mm.

The invention may further provide a kit for the treatment of anal and rectal fistula comprising a disposable, rectally-insertable, cannula including (e.g. a single dose of) activated carbon particles wherein 85% or more of the activated carbon particles have diameter in the range from 0.089 mm to 0.3 mm (e.g. wherein 85% or more of the activated carbon particles have diameter in the range from 0.152mm to 0.297 mm); and optionally an activation means that can be filled or loaded with a volume of driving fluid (e.g. liquid or gas such as air).

The disposable cannula may be removably-coupleable to the activation means such that the activation means is capable of driving a volume of the fluid (e.g. liquid) through the openable closure of the cannula and the cannula cavity to flush the dose of activated carbon out of the cannula cavity through the distal opening of the cannula. The kit may also comprise a supply of the driving liquid/fluid. Preferably, the kit comprises a plurality of rectally-insertable cannulas, each cannula being removably-coupleable to the activation means and each cannula being loaded with a single dose of activated carbon. Preferably the activated carbon is of average particle size 0.15 to 0.3 mm.

SPECIFIC EMBODIMENTS OF THE INVENTION

Specific embodiments of the invention will now be described with reference to the Figures in which:

FIG. 1 illustrates a device for delivering a dose of a pharmaceutical composition for use in the treatment of fistula according to an embodiment of the invention comprising activated carbon particles;

FIG. 2 illustrates a rectally-insertable cannula for use as a component part of the device illustrated in FIG. 1;

FIG. 1 illustrates a device 10 for delivering a dose of a pharmaceutical composition comprising activated carbon particles into a patient's rectal cavity. The patient has been diagnosed with a rectal or anal fistula by a medical professional (e.g. doctor) and has been assessed as being suitable for, and likely to be responsive to, such treatment. The device comprises a rectally-insertable cannula 20, a syringe 30, and a length of flexible tubing 40 coupling the syringe 30 to the cannula 20.

Figure 3:
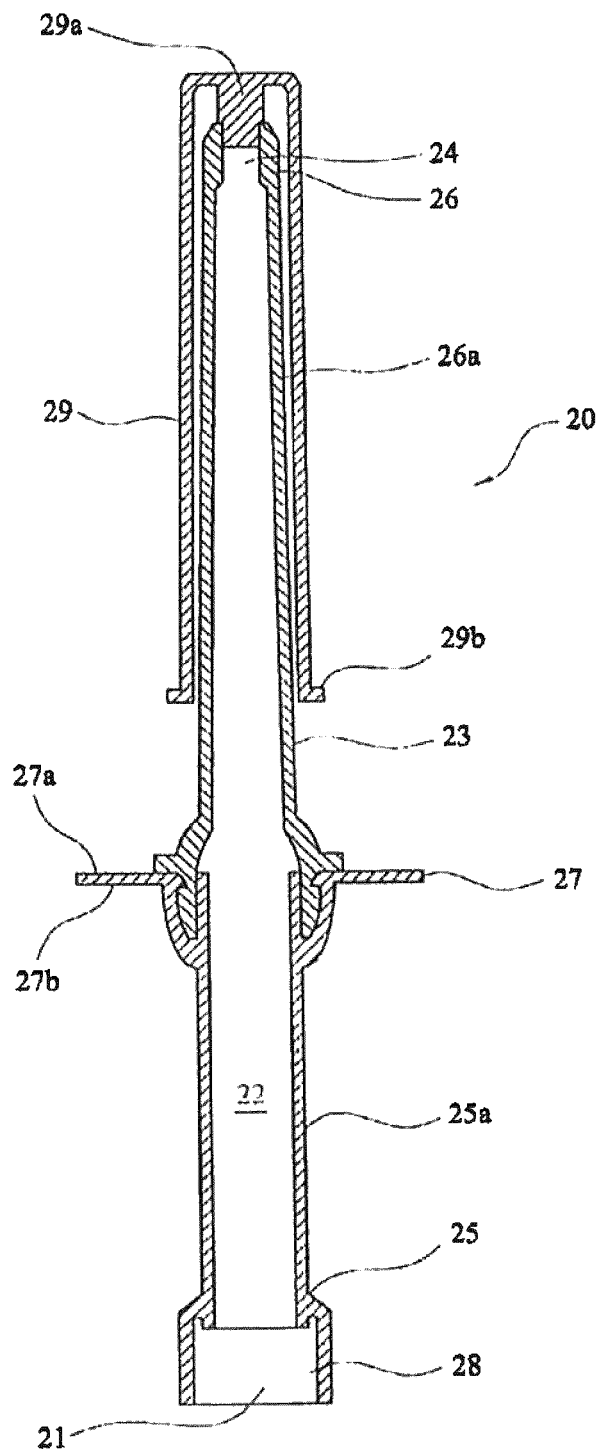
FIG. 3 illustrates a longitudinal cross-section of the rectally-insertable cannula of FIG. 2.

The cannula 20 is illustrated in greater detail in FIGS. 2 and 3. The cannula 20 has a generally elongated shape and has a proximal end 25 and a distal end 26. A cavity 22 is defined within a body 23 of the cannula 20, the cavity having a proximal opening 21 at the proximal end of the cannula leading into the cavity 22 and a distal opening 24 at the distal end of the cannula leading out of the cavity 22. The cavity 22 extends longitudinally between the proximal opening 21 and the distal opening 24.

The body 23 of the cannula 20 further defines a radially-extending flange or collar 27, which extends around a circumference of the cannula body 23 between the proximal end 25 and the distal end 26. A portion of the cannula body extending from the radially-extending flange toward the proximal end of the cannula may be termed a proximal portion 25a of the cannula body 23. Likewise, a portion of the cannula body 23 extending from the radially-extending flange 27 to the distal end 26 may be termed a distal portion 26a of the cannula.

In the specific embodiment described herein, the cannula is formed as a two-piece construction. Thus, the distal portion of the cannula body 26a and the proximal portion of the cannula body 25a are formed as separate polyethylene components and then joined together to form the cannula 20. The radially-extending flange is formed as part of the proximal portion of the cannula 25a, but could clearly be formed as part of the distal portion of the cannula 26a. The cannula may also be formed as a single component.

The distal portion 26a of the cannula is externally-sized and shaped to be inserted through a human anus into a human rectum in order to deliver the pharmaceutical composition into the patient's rectal ampulla. Accordingly, the distal portion 26a has a length of 7 cm and has a substantially circular external cross-section. The distal portion 26a is tapered at an angle of about 2° and has an outer diameter of 6.5 mm at the distal end 26. The radially-extending flange 27 has a substantially circular cross-section and a diameter of 3.0 cm. The proximal portion 25a of the cannula body 23 is also of substantially circular cross-section and tapers from an inner diameter of about 7.7 mm (outer diameter 15.5 mm) adjacent to the radially-extending flange to an inner diameter of about 6.3 mm (outer diameter 8.7 mm) at the proximal end 25 of the cannula.

The cavity 22 defined within the cannula body 23 extends longitudinally through the cannula body from the proximal end 25 to the distal end 26. At the distal end 26 the cavity terminates at the distal opening 24. The distal opening is of substantially circular cross-section and has a diameter of 2.8 mm. At the proximal end of the cannula the cavity 22 is spanned by a one-way valve (not shown). The diameter of the cannula at the proximal end is 6.3 mm. The one-way valve 50 is actuatable to allow fluids (e.g. liquids) to enter the cavity 22 through the proximal opening 21 of the cannula, but does not allow the passage of material contained within the cavity 22 of the cannula out of the cavity through the proximal opening 21. The cavity is about 120 mm in total length from the proximal opening to the distal opening. The cavity has a maximum diameter in the region of the radially-extending flange, where the internal cavity diameter is 7.7 mm. The volume of the cavity is about 2.6 $cm^3$, and the cannula is designed to be loaded with about 1.2 gram or about 1.3 gram of activated carbon particles having a bulk density of about 0.45 $g/cm^3$.

An upper surface 27a of the radially-extending flange 27 acts as a stop to prevent the cannula from being inserted too far into a patient's rectum. As the cannula is inserted to its maximum penetration depth, the upper surface 27a of the radially-extending flange abuts the patient's anus and prevents inadvertent over-penetration. It is clear that the radially-extending flange does not need to extend around the entire circumference of the cannula in order to perform this function. Any radially-extending projection that hinders passage of the cannula through the anus may be used if over-penetration is a concern.

A lower surface 27b of the radially-extending flange 27a may act as a lug that allows a user to apply an insertion-force in the direction of the distal end 26 of the cannula to facilitate its insertion.

The proximal end 25 of the cannula body 23 defines an internal cavity 28 in which a threaded linkage is pressed so as to allow the cannula to be coupled to a source of driving fluid (e.g. liquid). The thread is compatible with luer fittings as are well known in the medical profession. Luer fittings are commonly used to attach tubing and syringes and needles for medical use.

The internal surface of the cavity 22 is substantially cylindrical in cross-section and does not comprise any sudden changes in cross-section in order to minimise turbulence when a liquid is forced through the cavity 22.

In use, a pharmaceutical composition comprising activated carbon particles is contained within the cavity 22.

The pharmaceutical composition comprises 1.2 g activated carbon of average particle size 0.15 mm to 0.3 mm wherein 85% or more of the activated carbon particles have diameter in the range from 0.152 mm to 0.297 mm. The activated carbon is obtained from Chemviron Carbon tested to EUP 2010 Version 7.

The cavity 22 and the distal opening 24 are sized and shaped to optimise delivery of activated carbon particles having an average particle size of between 0.15 mm and 0.3 mm. Particles of this size range are easier to handle compared with fine activated carbon particles previously used for medical treatments and do not stick or agglomerate within the cavity to a great extent, which would hinder their delivery. As the particles are loaded within an elongated cavity that has a wide opening, the water entering the cavity through the one-way valve effectively acts to push the particles out of this opening. Preferably the water does not mix with the particles within the cavity (although some mixing is inevitable) but rather the front of the water entering through the valve pushes the cavity full of activated carbon particles ahead of it.

When loaded within the cavity 22, the activated carbon particles are prevented from escaping through the proximal opening 21 by means of the one-way valve 50 that spans the proximal opening. The distal opening 24 may also be closed by a closure means in order to retain the particles within the cavity 22. For example, the device may comprise a removable seal or a frangible seal spanning the distal opening 24. Alternatively or additionally, the device may comprise a cap that acts to close the distal opening 24 and, thereby retain any pharmaceutical composition within the cavity 22 until it is desired to use the device.

The cannula body is formed by an injection moulding process from a medical grade polyethylene. Polyethylene is a substantially inert material that is commonly used in medical devices. It is noted that the cannula may be formed from any suitable medical material and that the person skilled in the art would be aware of such material. For example the cannula may be made from a polyethylene, polupropylene or a polycarbonate or some other convenient medical grade polymer.

The syringe is a standard syringe having a liquid capacity of 12 ml, and comprises a plunger 31 that is slidable within a barrel 32. The syringe has a threaded luer-type connection 33, which allows the syringe to be coupled to the flexible tubing 40. The syringe acts as an actuation means of the device for driving a volume of liquid through the cannula cavity 22 to flush a dose of pharmaceutical composition contained within the cannula cavity.

is The flexible tubing 40 is formed from a flexible medical-grade polyvinyl chloride (PVC) and has an internal diameter of 2.6 mm, a length of 45 cm, and a capacity (i.e. the volume defined by the lumen of the tubing) of 2.4 ml. Each end of the flexible tubing terminates in a luer-type connection 41, 42. A first luer connection 41 allows the flexible tubing to be connected to the proximal end of the cannula 20 while a second luer connection 42, at the opposite end of the flexible tubing to the first luer connection 41, allows the flexible tubing to be connected to the syringe 30.

Figure 4:
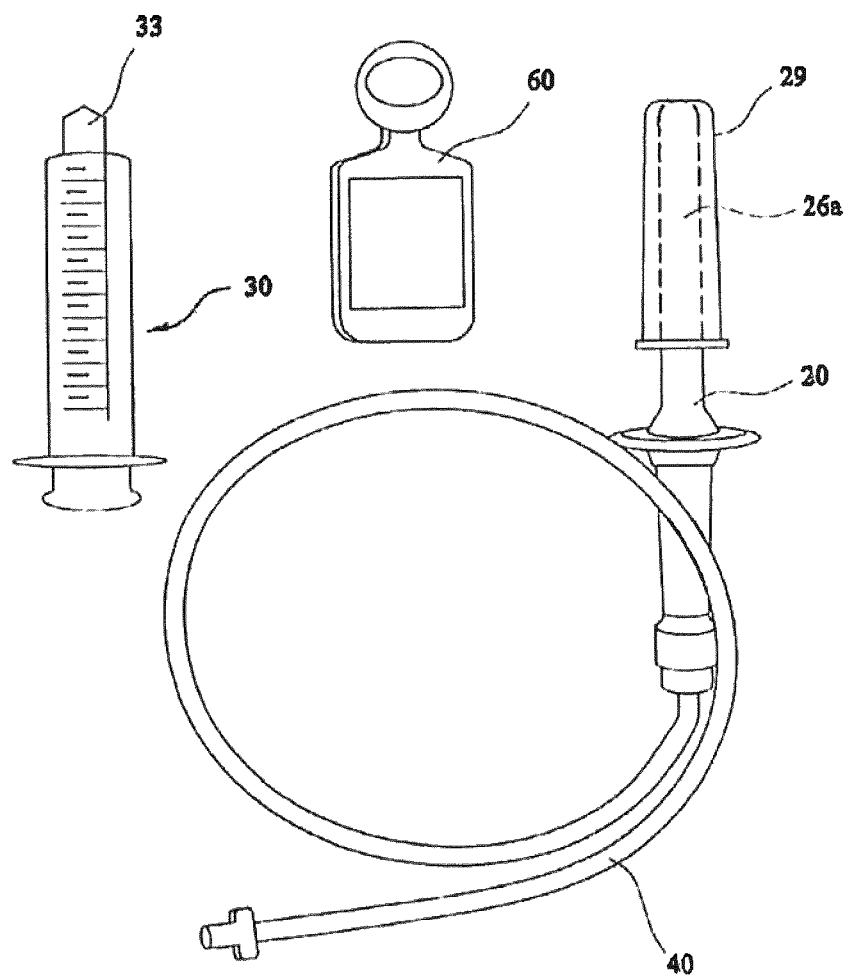
FIG. 4 illustrates a kit of parts for the treatment of rectal and anal fistulas comprising a device according to the embodiment of FIG. 1 and a source of sterile water.

It may be particularly convenient to supply a patient with both the device and any further elements that they need to self-administer a dose of a pharmaceutical composition comprising activated carbon particles. Thus, it may be advantageous to supply component elements of a device for delivering a dose of pharmaceutical composition and other materials in the form of a kit. An embodiment of such a kit is illustrated in FIG. 4. This kit includes component parts of a device as described above, i.e. a rectally insertable cannula 20, a syringe 30, and a length of flexible tubing 40 for connecting the syringe to the cannula (the flexible tubing is shown connected to the cannula). The kit also comprises a container filled with water for injection 60. The water for injection is used as a driving fluid to expel the pharmaceutical composition through the cannula and into the patient.

The kit may comprise other components. For example, the kit may include a supply of activated carbon for loading into the cannula. The kit may comprise a plurality of cannulas, each one pre-loaded with a dose of activated carbon.

In FIGS. 3 and 4, the cannula 20 is shown with its distal portion 26a sheathed within a cap 29. The cap comprises a stopper or bung 29a and a downwardly depending sheath 29b, and both sheaths the distal portion of the cannula 26a and closes the distal opening 24 thereby retaining medicament within the cannula.

The cannula is supplied pre-loaded with a pharmaceutical composition consisting of particles of activated carbon. The kit illustrated in FIG. 4 may be used to deliver a dose of a pharmaceutical composition comprising activated carbon particles as described below.

Figures 5, 6:
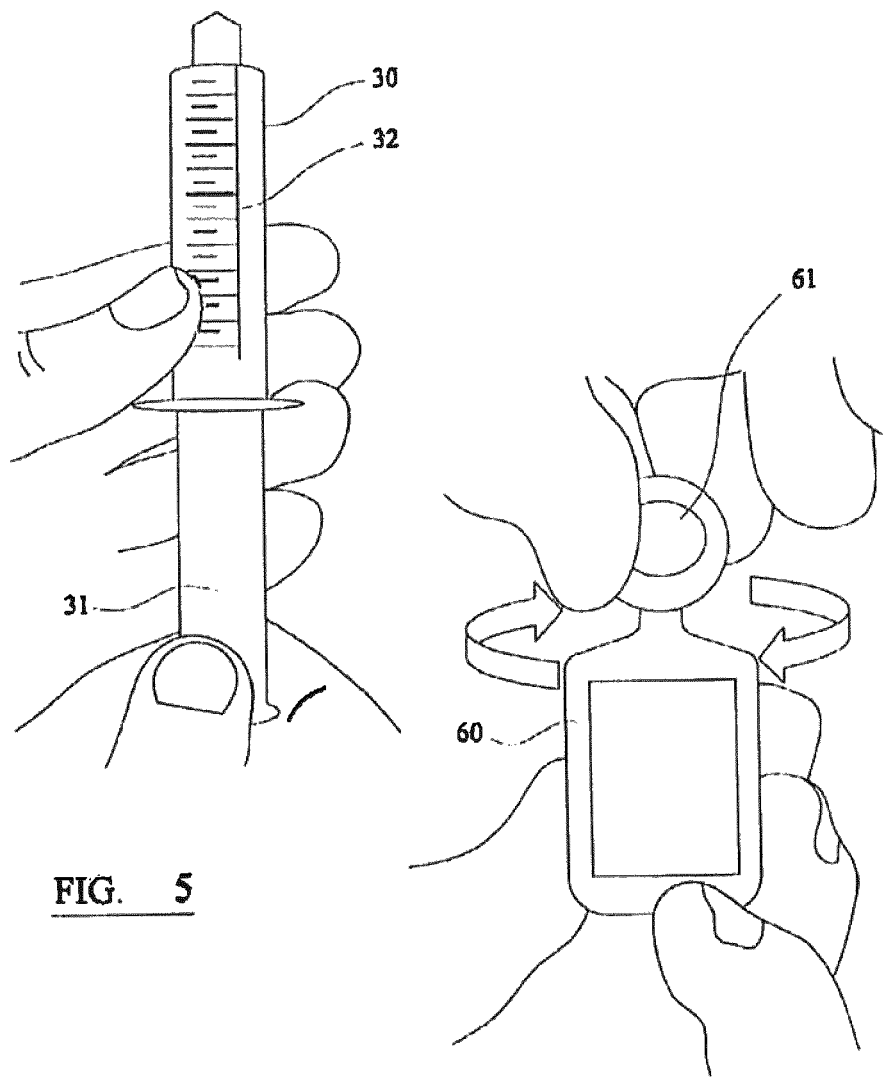
FIGS. 5 to 10 illustrate method steps involved in using the kit of FIG. 4.

FIGS. 5 to 10 illustrate a method of using the kit as illustrated in FIG. 4 in order to deliver a dose of activated carbon particles into a patient's rectal cavity. The individual component parts of the kit are removed from packaging in which they are supplied and set out before the user. The plunger 31 of the syringe 30 is withdrawn to the 11 ml marking on the barrel 32 of the syringe (as illustrated in FIG. 5). The user then removes a sealing cork 61 that acts to seal the container of water for injection 60 (illustrated in FIG. 6). The container of water 60 is maintained in an upright position so that its contents are not spilled.

The syringe 30 is coupled to the water container 60 in order to charge the syringe with water. The threaded luer connection 33 of the syringe engages with a corresponding mating thread in the neck 62 of the water container 60 (illustrated in FIG. 7).

Figures 7, 8:
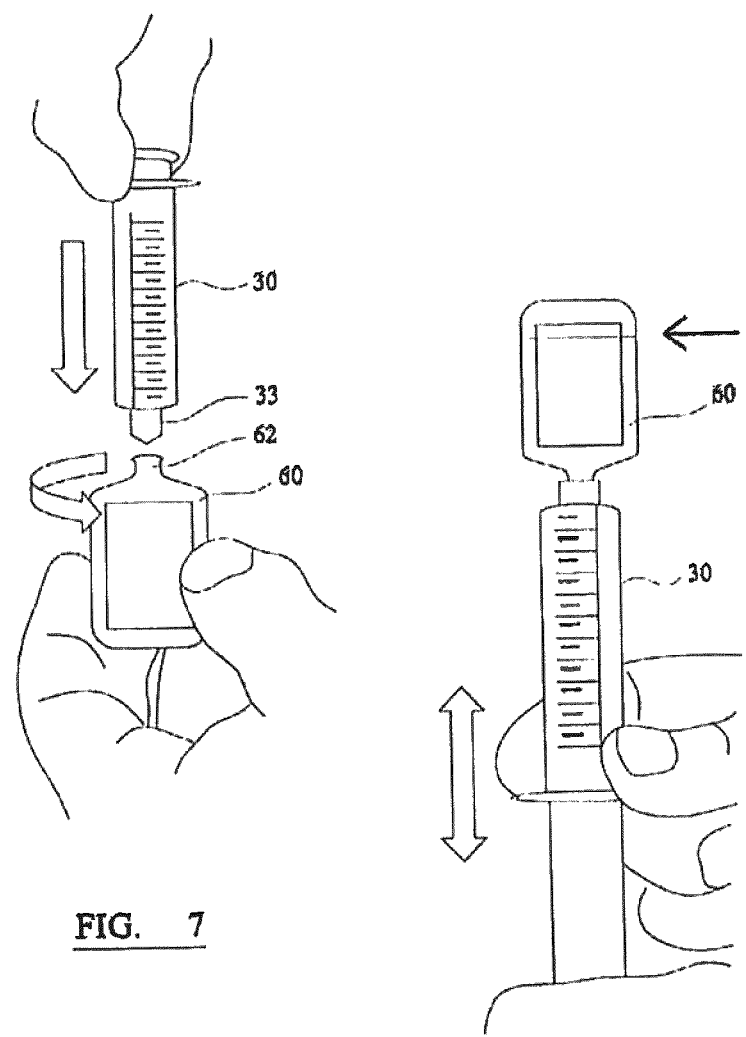
Figure 9:
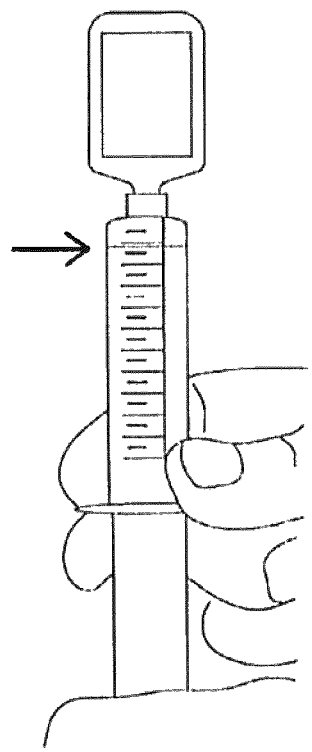

The water container 60, with the syringe now affixed, is inverted (illustrated in FIG. 8). The plunger 31 of the syringe 30 is then depressed to the 3 mm mark. This action causes air within the barrel of the syringe to be forced into the water container 60, which pressurises the container. The plunger is then withdrawn again. On withdrawal of the plunger, the water for injection passes into the barrel of the syringe. If required, the plunger can be repeatedly depressed and withdrawn. After these steps the barrel of the syringe should be filled with water for injection from the container of water 60 (this is illustrated in FIG. 9). Clearly, any technique for filling the syringe with the water may be used.

Figure 10:
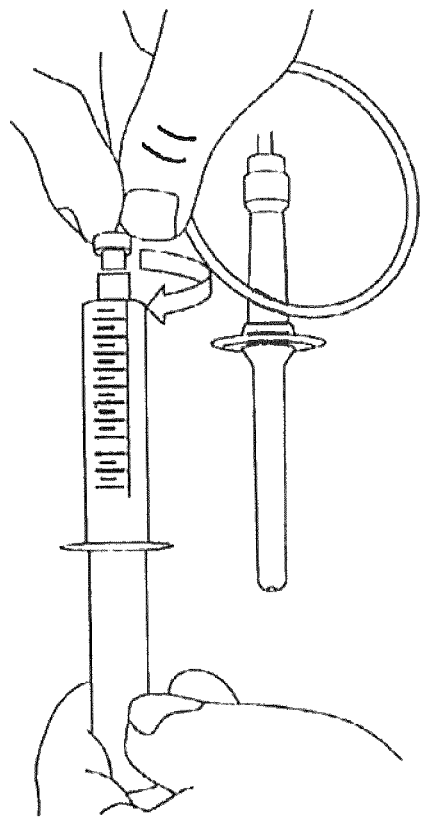

The cannula 20, which is preloaded with the pharmaceutical composition as described above, is coupled to the flexible tubing by screwing in the luer connections on the flexible tubing with equivalent connections on the cannula. Likewise, the flexible tubing is also connected to the syringe filled with water by coupling the luer connections on the flexible tubing and on the syringe (FIG. 10).

Immediately prior to use the cover or cap 29 is removed from the cannula 20. This opens the distal opening 24 such that the pharmaceutical composition can be forced out. If desired, the external surfaces of the distal portion 26a of the cannula may be lubricated, for example with petroleum jelly. Such lubrication may improve a patient's comfort on inserting the cannula. In some embodiments the distal portion of the cannula may be pre-lubricated. The distal portion 26a of the cannula 20 is then inserted carefully through the patient's anus so that the distal end 26 and the distal opening 24 enter the patient's rectal cavity. The cannula should be inserted until the radially-extending flange 27 abuts the anus and prevents further insertion.

With the cannula in place, the plunger 31 of the syringe 30 is pressed quickly. The plunger should preferably travel to its full extent over a period of no longer than 2 seconds. The water for injection contained within the barrel of the syringe is forced out of the syringe and through the flexible tubing 40, through the one-way valve 50 that closes the proximal opening 21 of the cannula and into the cannula cavity. On entering the cannula cavity 22, the flow of water forces the pharmaceutical composition that is contained within the cavity out of the cavity through the distal opening 24 and into the patient's rectal cavity.

After delivery of the pharmaceutical composition the cannula is removed from the patient's rectum. The cannula may then be cleaned, if it is to be re-used, or disposed of, if the device is only intended for one-time-use.

The device, kit, and method of using the device and kit as described herein refer to a specific embodiment. It is clear that many factors may be varied without changing the nature of the invention. For example, the embodiment described in detail above utilises a syringe as an actuation means for driving a volume of liquid through the cannula cavity. Any suitable actuation means may be used instead. For example, it may be possible to use a bellows or a bulb as an alternative to a syringe. In particular, it may be possible to replace the syringe with an automatic or motorised injection means for driving the volume of liquid.

The actual volume of liquid injected, and therefore the size of the syringe, may be varied. For example, such variation may be desirable if the volume of the cannula cavity is larger or smaller than the embodiment described above, or if the length of flexible tubing is longer or shorter. The volume of liquid should be sufficient to drive the entire contents of the cannula into the patient's rectum without delivering an excessive volume of liquid to the patient.

Although the embodiment described above uses flexible tubing disposed between the syringe and the cannula, other embodiments may dispense with the flexible tubing and provide a direct connection between the cannula and syringe or other means for driving the volume of liquid.

The size and shape of the cannula may be varied from the dimensions described in the embodiment above. Different sized cannulas may, for example, allow different volumes of pharmaceutical composition to be dispensed to a patient.

As set out above, the applicants have found that if the activated carbon is of particle size 0.15 mm to 1 mm, a liquid (e.g. water) should be used as driving fluid to deliver the dry powder. The applicants have surprisingly found that if the activated carbon is of particle size 0.05 mm to 0.15 mm, the fluid (driving fluid) may be either a liquid (e.g. water, as above) or a gas (e.g. air).

EXAMPLE 1

An Open Prospective Study Evaluating the Efficacy and Safety of Activated Carbon for the Treatment of Chronic, Non-complicated Perianal Fistulas Background The activated carbon was administered using the device described above and illustrated in the attached Figures.

Spontaneous fistula healing rates are considered to be very low, of the order of 4 to 5% (clinical experience of the participating investigators). For saftey, a value of 10% was used in setting up the trial (e.g. for the subject number calculation) meaning that an uncontrolled design could be selected as the preferred design for this initial pilot trial. This design allows for a preliminary indication of effect.

Clinical assessment of fistula healing (healed/not healed), was selected as the primary endpoint since this is the endpoint used in daily clinical practice. Rectal ultrasound evaluations were also made because these can provide more detailed measures of the degree of healing as compared to the clinical evaluation (healed/not healed).

The secondary endpoints are less established, but still of importance to the evaluation of benefit/effect. It is very important to measure if the patient feels any improvement but there are no validated tools available to measure patient reported outcome in perianal fistulising disease. In this study, a VAS scale was used to assess pain and soiling, and a questionnaire was used to evaluate the impact on daily function, and also perception of ease of use.

Dose and Timing

The dose administered by the medical device in the trial was 2.6 g/day. In order to provide as much activated carbon to the affected areas as possible the device was used twice daily (with at least 6 hours in between administrations); thus, the device was used to administer activated carbon at a dose of 1.3 g twice daily.

The dose was administered by the patient in the morning: after breakfast (after defecation), and in the evening, prior to "going to bed".

A treatment period of 8 weeks was chosen. Since the main problem with all existing treatment modalities is the high recurrence rates (20-60%), it is relevant to perform a follow up visit. In this study the follow-up visit was scheduled to be performed at least 4 months after the last administration.

Selection of the Trial Population

For this initial trial in perianal fistulas a population with few complications and low, more easily accessible, location was selected. Thirty patients were selected. The recruitment of patients was performed as described below:

1. Patients who have symptoms from their fistulas and were referred or contacted the site themself were offered an opportunity to participate in the trial.
2. Following review of patient records/data bases patients were contacted and asked to participate in the trial.

The inclusion criteria for the trial are as follows:

1. Patients with perianal fistulas diagnosed by clinical examination and evaluated as "not healed/open"

2. Fistula classified as intersphincteric and transsphincteric according to Parks'classification 3. Superficial fistula involving a part of the external sphincter muscle
4. Age: ≥18 years and ≤75 years
5. Informed consent and/or Letter of Authority (as applicable) obtained The exclusion criteria were as follows:
6. Inflammatory Bowel Disease (IBD)
7. Rectovaginal fistulas
8. Rectouretral fistulas
9. Rectovesical fistulas
10. Extra-sphincteric and supra-sphincteric fistula according to Parks'classification
11. Complicated fistulas (eg. horse shoe fistulas) as evaluated by the investigator.
12. Any previous surgical treatment for perianal fistulas
13. Subcutaneous fistulas not involving any part of the external sphincter
14. Colorectal and/or anal malignancy
15. Other malignancy requiring active treatment
16. Other diseases which as per the investigator's opinion should be contraindicated
17. Subjects who are not able to complete study procedures as per the investigator's opinion There are no restrictions in the therapy received prior to this trial. Anti inflammatory therapies (as NSAIDs), antibiotics or immunomodulatory concomitant therapies (including corticosteroids, metronidazole and anti TNFα therapy) were not allowed during the trial. Any other therapy for the fistula was avoided during participation in the trial.

The Investigational Medical Device (IMD) is illustrated in the the attached drawings (see especially FIGS. 1 and 4) and consisted of:
1. Rectal cannula set
a. Rectal cannula with cap, valve and carbon chamber
b. Connection tube with female connector
c. Vaseline plug (soft yellow paraffin/vaselinum flavum)
d. Activated carbon 1.3 g (for injection into the rectum)
2. Sterile water (Ph. Eur. Quality) 10 ml in plastic container
3. Sterile syringe (CE-marked)—10 ml All medical devices are provided by Nordic Drugs AB. Subjects were trained in the use of the device by the investigator or a nurse. The activated carbon (Activated Carbon 610C (EUP 2010) was administered using 10 ml. sterile water (Fresenius Kabi) by means of a sterile syringe (BRAUN lnjekt, CE marked), by the method described above.

All medicinal device components were handled according to the principles of Good Manufacturing Practice and applicable ISO guidelines.

Trial Procedure
Day 1/Baseline

On day 1, consent was obtained and the patient instructed in how to use the device. The investigator performed an overall assessment of the patients state of health in order to confirm eligibility. Except for digital rectal examination and the clinical evaluation of the fistula no examinations are required. A rectoscopy was performed in order to rule out malignancies and high located fistulas. Samples were taken and sent to the local laboratory to be ananlysed for: CRP, Hb and WBC.

A clinical evaluation of fistula anatomy was made by anal ultrasonography.

The Form for Patient Assessment of Symptoms and Impact on Daily Function was handed out to patient and completed at the visit.

Week 2 (Telephone Visit):

By telephone interview the patients were asked if they had used the Medical Device; patients are asked if they have experienced any problems with the device and if they have observed any adverse events.

Week 8 (End of Intervention)

The investigator performed an overall assessment of the patients state of health in order to observe any possible changes (=Adverse events) not already reported by the patient. Except for digital rectal examination and the clinical evaluation of the fistula no examinations were performed.

Patients were asked if they have experienced any problems with the device and if they have observed any adverse events.

A rectoscopy was performed. Samples were taken and sent to the local laboratory to be ananlysed for: CRP, Hb and WBC.

A clinical evaluation of fistula closure was made by anal ultrasonography (for fistula healing and type). The Form for Patient Assessment of Symptoms and Impact on Daily Function was handed out to patient and completed at the visit. Medical Device patient acceptability/performance questions were asked.

Week 24 (Follow-up)

A medical examination was made (digital rectal examination only), together with clinical evaluation of fistula closure by anal ultrasonography (fistula healing and type). The Form for Patient Assessment of Symptoms and Impact on Daily Function is handed out to patient and again completed at the visit.

Assessments and Results

The primary endpoint was clinical assessment of fistula healing (healed/not healed). Healing was defined as the fistula closed and no secretion as observed by visual inspection.

A rectoscopy was performed, and the result given on a scale of 1 to 5 (1=ulcerations, 2=fistula, 3=Abscess, 4=Stenosis, 5=fissure).

A Form for Patient Assessment of Symptoms and Impact on Daily Function was handed out to the patients. A 10 point VAS scale was be used to assess pain and soiling (0=no pain/soiling, 10=unbearable pain/soiling). In additions a questionnaire was used to assess the impact on daily function. The patients were also asked the following questions relating to the Medical Device at study end:
1 Would you like to use KULIST again?
   If the answer is no: please explain why
2 Describe advantages and disadvantages of the device
3 Have you had any difficulties in using the device
4 Could the device be more user friendly? How?

Results

The following preliminary results are based on week 8 (end of intervention) data from 26 of the 28 enrolled patients.

Data on the primary endpoint, healing, indicates that over 30% (30.7%) have complete healing (fistula closed, no discharge). The confidence interval (data not shown) indicates the results are of statistical significance. This is a spectacular improvement on the spontaneous healing rate assessed by the clinic (4 to 5%), and is indicative that this treatment may provide a real alternative to surgery.

Oral communcation with the test sites have reveiled that at least 2 other patients have, in addition experienced, improvements and signs of healing such as reduced soiling.

The patients generally found the rectal system to be easy to operate.

The only adverse event observed (1 patient) was constipation. There were no side effects or adverse events from the device itself reported. Thus, the use of rectally administered activated carbon (of specific size) is effective and avoids the drawbacks of previous methods, and the risks associated with surgical intervention.

EXAMPLE 2

The activated carbon was administered using the device described above and illustrated in the attached Figures.

Activated carbon of particle size 0.05 to 0.15 mm (mesh size 100×270 US mesh) was administered using air (instead of water) as the propellant/fluid. The applicants found that administration was effectively administered rectally, with air as the propellant. The applicants also found that activated carbon of particle size 0.05 to 0.15 mm (mesh size 100×270 US mesh) was effectively administered using water as the propellant/fluid.

The invention claimed is:

1. A method for the treatment of fistula, the method comprising administering to a subject in need of such treatment a pharmaceutically effective amount of a composition consisting of particles of activated carbon, wherein the activated carbon is administered rectally as a dry dose, and wherein the activated carbon is driven into the rectum of the subject using a driving fluid.

2. A method according to claim 1, wherein the activated carbon is of average particle size 0.05 mm to 1 mm.

3. A method according to claim 1, wherein the activated carbon is of average particle size 0.15 mm to 1 mm.

4. A method for the treatment of fistula, the method comprising administering to a subject in need of such treatment a pharmaceutically effective amount of a composition consisting of particles of activated carbon wherein 85% or more of the activated carbon particles have diameter in the range from 0.089 mm to 0.3 mm, wherein the activated carbon is administered rectally as a dry dose, and wherein the activated carbon is driven into the rectum of the subject using a driving fluid.

5. A method according to claim 4, wherein 85% or more of the activated carbon particles have diameter in the range from 0.152 mm to 0.297 mm.

6. A method according to claim 1, wherein the fistula is rectal fistula.

7. A method according to claim 1, wherein the amount of activated carbon administered is in the range from 450 µg to 10 g.

8. A method according to claim 1, wherein the activated carbon is granular.

9. A method according to claim 1, wherein 90% or more of the activated carbon particles have diameter in the range from 0.125 mm to 0.297 mm.

10. A method according to claim 1, wherein 85% or more of the activated carbon particles have diameter in the range from 0.152 mm to 0.297 mm.

11. A method for the treatment of fistula, the method comprising administering to a subject in need of such treatment a composition consisting of a dry powder of activated carbon which is dust free, wherein the composition is administered rectally as a dry dose, and wherein the activated carbon is driven into the rectum of the subject using a driving fluid.

12. A method for the treatment of fistula, the method comprising administering to a subject in need of such treatment a composition consisting of a dry powder (a dry dose) of activated carbon of particle size 0.001 to 1 mm, wherein the composition is administered rectally, and wherein the activated carbon is driven into the rectum of the subject using a driving fluid.

13. A method according to claim 1, wherein the activated carbon is of average particle size 0.02 to 1 mm.

14. A method according to claim 1, wherein the activated carbon is of average particle size 0.15 mm to 0.3 mm.

15. A method according to claim 1, wherein the fistula is anal fistula.

16. A method according to claim 1, wherein the activated carbon is ground activated carbon having an irregular particle shape.

17. A method according to claim 1, wherein the composition is administered using a disposable, rectally-insertable, cannula containing the composition.

18. The method of claim 1, wherein the driving fluid is a liquid.

19. The method of claim 18, wherein the driving fluid is water.

20. The method of claim 1, wherein the driving fluid is a gas.

21. The method of claim 20, wherein the driving fluid is air.

22. The method of claim 18, wherein the activated carbon is of particle size 0.15 mm to 1 mm.

23. The method of claim 19, wherein the activated carbon is of particle size 0.15 mm to 1 mm.

24. The method of claim 18, wherein the activated carbon is of particle size 0.05 mm to 0.15 mm.

25. The method of claim 19, wherein the activated carbon is of particle size 0.05 mm to 0.15 mm.

26. The method of claim 20, wherein the activated carbon is of particle size 0.05 mm to 0.15 mm.

27. The method of claim 21, wherein the activated carbon is of particle size 0.05 mm to 0.15 mm.

28. The method of claim 1, wherein the treatment comprises closing the fistula.

29. The method of claim 1, wherein the treatment comprises healing the fistula, wherein the healing comprises closing the fistula without discharge.

30. The method of claim 1, wherein the activated carbon is administered twice daily.

31. The method of claim 30, wherein the activated carbon is administered once in the morning and once in the evening.

32. The method of claim 30, wherein the treatment comprises closing the fistula within eight weeks of commencing treatment.

33. The method of claim 1, wherein the driving fluid is maintained separately from the driving fluid until immediately before the activated carbon is administered.

34. A method for the treatment of fistula in a subject in need thereof, the method comprising providing a device containing a formulation that consists of particles of activated carbon as a dry dose, and further contains the driving fluid maintained separately from the activated carbon; inserting the device into the rectum of the subject; and actuating the device to cause the activated carbon to be driven into the rectum of the subject by the driving fluid.

35. The method of claim 34, wherein the activated carbon is of particle size 0.15 mm to 1 mm and the driving fluid is a liquid; or wherein the activated carbon is of particle size 0.05 mm to 0.15 mm and the driving fluid is a liquid or a gas.

36. The method of claim 35, wherein the driving fluid is a liquid.

37. The method of claim 36, wherein the driving fluid is water.

38. The method of claim 35, wherein the driving fluid is a gas.

39. The method of claim 38, wherein the driving fluid is air.

40. The method of claim 1, wherein the treatment is continued for a period of at least 8 weeks.

41. The method of claim 40, wherein the activated carbon is administered twice daily during the treatment period.

\* \* \* \* \*